dyeable stratum in those integral film units, e.g., on the side of the dyeable stratum opposed from the negative components, they may, if desired, be associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing fluid.

As is now well known and illustrated, for example, in the previously cited patents, the liquid processing composition referred to for effecting multicolor diffusion transfer processes comprises at least an aqueous solution of an alkaline material, for example sodium hydroxide, potassium hydroxide, and the like, and preferably possessing a pH in excess of 12, and most preferably includes a viscosity-increasing compound constituting a film-forming material of the type which, when the composition is spread and dried, forms a relatively firm and relatively stable film. The preferred film-forming materials comprise high molecular weight polymers such as polymeric, water-soluble ethers which are inert to an alkaline solution such as, for example, a hydroxyethyl cellulose or sodium carboxymethyl cellulose. Other film-forming materials or hickening agents whose ability to increase viscosity is substantially unaffected if left in solution for a long period of time also are capable of utilization. The film-forming material is preferably contained in the processing composition in such suitable quantities as to impart to the composition a viscosity in excess of 100 cps, at a temperature of approximately 24° C. and preferably in the order of 100,000 cps to 200,000 cps at that temperature.

In particularly useful embodiments, the transparent polymeric support contains a small quantity of a pigment, e.g., carbon black, to prevent fog formation due to lightpiping by internal reflection within the transparent support, and subsequent exiting from the support surface carrying the photographic layers, of actinic light incident upon an edge thereof; such elements are described in Belgian Pat. No. 777,407. The transparent support advantageously may include an ultraviolet light absorber.

For purposes of illustrating the invention, a solution of a sample of the compound of Example 1 was incorporated into the image-receiving layer 3 of an image-receiving component comprising the structure set forth below by mixing the solution of the compound with a solution of the graft copolymer and coating this mixture on top of the timing layer to complete the image-receiving component.

A transparent 4 mil polyethylene terephthalate film base coated with, in succession:

1. as a polymeric acid layer, a mixture of about 9 parts of a partial butyl ester of polyethylene/maleic anhydride copolymer and 1 part of polyvinyl butyral coated at a coverage of about 2,500 mgs./ft.$^2$;

2. a timing layer containing a 14:1 ratio of a 60-30-4-6 tetrapolymer of butylacrylate, diacetone acrylamide, styrene and methacrylic acid and polyvinyl alcohol at a coverage of 500 mgs./ft.$^2$;

3. a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs./ft.$^2$ to provide an image-receiving layer and containing the selected dye compound at a coverage of 11 mgs./ft.$^2$. (Dye particles were present in the coating.)

The image-receiving component containing the dye compound was placed on a piece of gelatin coated Mylar, and the transmission densities for red (R), green (G) and blue (B) were recorded on a transmission densitometer. Then several drops of aqueous 1 N KOH were added to the gelatin sheet, and the image-receiving component was lightly pressed against the gelatin sheet to "bleach" the dye compound. After about 60 seconds, the transmission densities were again recorded for red (R), green (G) and blue (B) for the "sanwich". The results are set forth below.

| Transmission Densities | | | | | |
|---|---|---|---|---|---|
| Before Bleaching | | | After Bleaching | | |
| R | G | B | R | G | B |
| .19 | .06 | .05 | .02 | .00 | .02 |

The densitometer was set at 0.00 for R, G, B with two pieces of gelatin coated Mylar in the light beam.

From these results, it can be seen that the subject dyes are effective in absorbing radiation within a certain wavelength range, and when treated with aqueous alkali are "bleached", i.e., decolorized.

It will be appreciated that various solvents may be employed for dispersing the dyes in the image-receiving or other appropriate layer of the photographic product and that useful solvents may be readily selected for a given compound. Also, it will be understood that where the anion may possibly have an adverse effect on the photosensitive material, the dye will be positioned other than in the silver halide emulsion layer(s), and depending upon the mobility of the dye in a given matrix or binder, it may be desirable to employ an immobilizing group or a group that will mordant to the matrix to prevent migration of the dye, particularly, where the photographic product is subjected to conditions of high temperature and high humidity prior to use.

Also, it will be appreciated that in utilizing the subject dyes to correct color balance, for example, in multicolor diffusion transfer photographic film units that a photosensitive element may be exposed to a suitable multicolor step-wedge and diffusion transfer processed with a given processing composition and image-receiving element. The blue, green and red D log E curves of the resulting multicolor transfer image (sample image) are then prepared. Examination of these D log E curves will indicate to one skilled in color photographic sensitometry the manner and extent to which the individual D log E curves depart from the desired curve shape. From this examination, one may determine by routine analysis and experimentation how much filtration would be required of what wavelength range or ranges to obtain a more desirable color balance. The photosensitive element of another film unit, having the identical photosensitive element, image-receiving element and processing composition as used in obtaining the sample image, is then given the same exposure through a conventional color correction filter(s) of the color and density estimated to be necessary to provide the desired changes in the D log E curves of the sample image. The blue, green and red D log E curves of the resulting test multicolor transfer image are then prepared and compared with the sample. While more than one "test" may be required to determine the color filtration most effective to give the desired D log E curve shape changes, such tests may be performed rapidly and easily. When

ARYL-1-MERCAPTOALKANOYLPROLINE AND HOMOPROLINE DERIVATIVES

BRIEF DESCRIPTION OF THE INVENTION

The compounds of this invention, certain aryl-1-mercaptoalkanoyl-homoproline and aryl-1-mercaptoalkanoyl-proline derivatives and their cyclized thiazadione heterocyclic analogues, reduce blood pressure in animals. They function as inhibitors of angiotensin converting enzyme in that they block C-terminal cleavage of the histidyl[9]-leucine[10] dipeptide from angiotensin I, thereby decreasing conversion to the strong pressor octapeptide antiotensin II.

DETAILED DESCRIPTION OF THE INVENTION

In accordance with this invention there is provided a group of hypotensive agents of the formula:

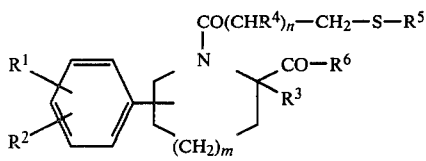

wherein
$R^1$ and $R^2$ are, independently, hydrogen, alkyl of one to six carbon atoms, alkoxy of one to six carbon atoms, or halo;
$R^3$ is hydrogen or alkyl of one to six carbon atoms;
$R^4$ is hydrogen or alkyl of one to six carbon atoms;
$R^5$ is hydrogen, alkanoyl of two to six carbon atoms or aroyl of six to ten carbon atoms;
$R^6$ is —OH or —OM where M is a pharmaceutically acceptable cation;
m is one of the integers 0 or 1;
n is one of the integers 0, 1 or 2;
and the correspondingly substituted thiazadione derivatives of the formula

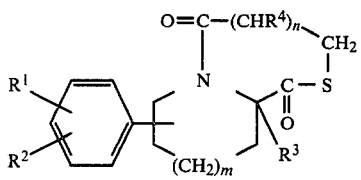

The preferred compounds of the invention are those of the preceding formulae in which $R^1$ and $R^2$ are, independently, hydrogen or alkoxy of one to three carbon atoms (the most preferred alkoxy substituent is methoxy); $R^3$ is hydrogen or methyl; $R^4$ is hydrogen or alkyl of one to three carbon atoms; $R^5$ is hydrogen, acetyl or benzoyl; $R^6$ is —OH or —OM where M is sodium, potassium or $NH_4$; m is zero; n is one; and the substituted phenyl moiety is ortho to the ring nitrogen atom or to the ring carboxy substituent. The halo substituent representing $R^1$ or $R^2$ may be chlorine, bromine, iodine or fluorine; chlorine or bromine being preferred.

The pharmaceutically acceptable cations representing M are those derived from bases which yield a pharmaceutically acceptable salt of the open ring compounds. The salts may be derived from either inorganic or organic bases to yield ammonium salts; alkali metal salts (sodium, potassium, etc.); alkaline earth salts, preferably calcium or magnesium; dicyclohexylamine salts, lower alkylamine salts; di(lower)alkylamine salts; tri(lower)alkylamine salts and the corresponding omega-hydroxy analogues (e.g. methylamine, ethylamine, propylamine, dimethylamine, diethylamine, dipropylamine, trimethylamine, triethylamine, tripropylamine, di(hydroxyethyl)amine, and the like). Similarly more complex amines which are employed in depot administration for slow release into the body, such as $N,N^1$-dibenzylethylenediamine, are applicable bases for pharmaceutically acceptable salt formulation.

The compounds of this invention are produced by acylation of the aryl substituted 2-carboxy-heterocyclic amine precursor of the formula:

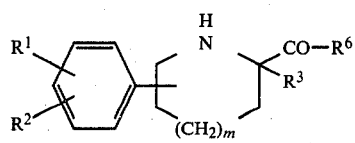

where $R^1$, $R^2$, $R^3$, $R^6$ and m are defined above, in aqueous alkaline solution with a substituted alkanoic acid halide of the formula:

$$XCO(CHR^4)_n CH_2 Y$$

where
X is chloride or bromide;
$R^4$ and n are defined above and
Y is chloro, bromo, alkanoylthio of 2 to 6 carbon atoms or aroylthio of 6 to 10 carbon atoms.
Where Y is chloro or bromo, the intermediate product is reacted with an alkali metal salt of a thioalkanoic acid or thioaromatic acid to introduce the mercapto function in the terminal position represented by Y.

Ring closure between the 2-carboxyl group and the mercapto substituent representing Y is accomplished by conventional activation of the carboxyl group, e.g. as an activated ester, mixed anhydride, carbodiimide, acyl halide, etc. The use of N, $N^1$-dicyclohexylcarbodiimide (DCC) is a preferred activating reagent because of the facility of the ring closure and ease of removal of the dicyclohexyl urea by product.

The compounds of this invention contain two chiral centers in the nitrogen containing heterocyclic ring, specifically the carbon atom to which the carboxy substituent is attached (α-carbon of proline) and the carbon atom to which the phenyl substituent is attached (either the β or δ-carbon of proline). Hence, by selection or preparation of a proline or homoproline reactant of known relative stereoconfiguration, the final product obtained is limited to a dl-mixture of stereoisomers-(epimers) which are separable by standard methods of resolution when the reactant $XCO(CHR^4)_n CH_2 Y$ contains no additional chiral center (i.e., $R^4$ is hydrogen). Where the alkanoic acid halide $XCO(CHR^4)_n CH_2 Y$ contains a chiral center, i.e. $R^4$ is other than hydrogen, diastereisomers are formed which are readily separated by conventional methods such as fractional crystallization, chromatography or fractional distillation.

The pharmaceutically acceptable salts of the 3-carboxy isoquinoline compounds are produced in a conventional manner by neutralization of the acid with an equivalent of the desired base.

The starting compounds for production of the compounds disclosed herein are either known or readily tered off it was dissolved in methylene chloride, washed with brine, dried over sodium sulfate and the solvent evaporated off to give the title compound as a white solid, m.p. 69°-73° C.

Analysis for: $C_{16}H_{21}NSO_5.0.5\ CH_2Cl_2$: Calculated: C, 51.83; H, 5.80; N, 3.66. Found: C, 52.07; H, 5.68; N, 3.78.

EXAMPLE 3 cis-1-(3-Benzoylthiopropanoyl)-5-phenyl proline

To a solution of cis-5-phenyl proline hydrochloride (5.0 g., 0.022 m) and 1 N sodium hydroxide (44 ml.) at 10° C. was slowly added 3-bromopropionyl chloride (2.2 ml., 0.022 m) and 2-N sodium hydroxide (11 ml.), keeping pH between 7.5 and 9. The mixture was stirred at 25° C. for 3 hours. Potassium thiobenzoate, prepared by mixing thiobenzoic acid, 95% (3.28 g., 0.024 m) and potassium carbonate (2.02 g., 0.014 m) in water (25 ml.), was added to the reaction, which was stirred overnight at 25° C. The solution was acidified and extracted with ethylacetate. The extract was washed, dried over sodium sulfate and the solvent was evaporated off to yield the title compound as a gum which was employed as the reactant in the following example without further purification.

EXAMPLE 4 cis-1-(3-Mercaptopropanoyl)-5-phenyl proline

This product from Example 3 was added to a solution of methanol saturated with ammonia and was stirred at 25° C. for 2 hours. The solvent was evaporated off, leaving a solid which was stirred in water and filtered. The filtrate was extracted five times with diethyl ether and was acidified. The acidified solution was then extracted with methylene chloride, washed with brine, dried over magnesium sulfate and concentrated to a solid. This residue was extracted with hot hexane from which the title compound crystallized, m.p. 61°-64° C.

Analysis for: $C_{14}H_{17}NSO_3$: Calculated: C, 60.19; H, 6.14; N, 5.02. Found: C, 60.34; H, 5.99; N, 5.04.

EXAMPLE 5 trans-Hexahydro-7(3,4-dimethoxyphenyl)-1H,5H-pyrrolo[2,1-c][1,4]thiazepine-1,5-dione The compound produced in Example 2 is dissolved in about 500 milliliters methylene chloride and the solution is chilled under nitrogen to 15° C. in a dry ice-acetone mixture. 4-Dimethylaminopyridine is added and the mixture is stirred for five minutes. A slight excess of dicyclohexylcarbodiimide dissolved in methylene chloride is added with stirring. The chilled source is removed after 15 minutes and the solution is stirred overnight at room temperature. The volume of the reaction mixture is reduced on a rotary evaporator under reduced pressure to about 100 milliliters. A precipitate is removed by filtration and the filter residue is washed several times with methylene chloride. The filtrate and combined washings are washed successively with 1 N HCl, saturated aqueous $NaHCO_3$, water and saline and the solution is dried over $MgSO_4$. Evaporation of the methylene chloride with a rotary evaporator under reduced pressure yields the title compound.

EXAMPLE 6 trans-Hexahydro-7-phenyl-1H,5H-pyrrolo[2,1-c][1,4]thiazepine-1,5-dione

Following the procedure of Example 5 with the exception that the reactant to be cyclized is the product of Example 4, affords the title compound.

EXAMPLE 7

α-and γ-5-Phenyl-1-(3-benzoylthio-2-methyl-1-oxopropyl)-proline

To a solution of cis-5-phenyl proline hydrochloride (30.0 g., 0.13 m) and sodium hydroxide (10.4 g., 0.26 m) in water (600 ml.) at 10° C. was slowly added (−) 3-benzoylthio-2-methyl propionyl chloride (31.42 g., 0.13 m). At the same time, from a separate dropping funnel, was added a solution of sodium hydroxide (5.2 g., 0.13 m) in water (70 ml.) at such a rate that the solution was maintained at a pH between 9.5 and 7.5 pH units (final pH 7.5). After stirring overnight at 5° C., the reaction mixture was filtered and the clear filtrate acidified with dilute hydrochloric acid. The product was extracted into diethyl ether. A solid (2.65 g) precipitated from the ether extract. This material was recrystallized from acetonitrile, giving the α-acid as a white solid, m.p. 194°-195° C., $[\alpha]_D^{24.5}=O$, (C=93%, MeOH).

Analysis for: $C_{22}H_{23}NSO_4$: Calculated: C, 66.47; H, 5.83; N, 3.52. Found: C, 66.30; H, 5.86; N, 3.60.

The diethyl ether filtrate was washed with brine, dried over anhydrous sodium sulfate and filtered. A white solid crystallized from the ether solution, 5.60 g. The product was recrystallized from acetonitrile to give the β-acid m.p. 148°-149° C, $[\alpha]_D^{24.5}=O$ (C=0.78%, MeOH).

Analysis for: $C_{22}H_{23}NSO_4$: Calculated: C, 66.47; H, 5.83; N, 3.52. Found: C, 65.96; H, 5.79; N, 3.79.

EXAMPLE 8

α-and β-5-phenyl-1-(3-mercapto-2-methylpropanoyl) proline

Each of the compounds of Example 7 is treated with ammonium hydroxide and worked up in accordance with the procedure of Example 2 to afford the title compound.

What is claimed is:

1. A compound of the formula:

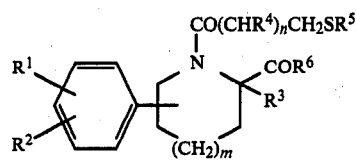

wherein
$R^1$ and $R^2$, are independently, hydrogen, alkyl of one to six carbon atoms, alkoxy of one to six carbon atoms or halo;
$R^3$ is hydrogen or alkyl of one to six carbon atoms;
$R^4$ is hydrogen or alkyl of one to six carbon atoms;
$R^5$ is hydrogen, alkanoyl of two to six carbon atoms or benzoyl;
$R^6$ is —OH or —OM where M is a pharmaceutically acceptable cation;
m is one of the integers 0 or 1; and n is one of the integers 0, 1 or 2.

2. A compound of the formula:

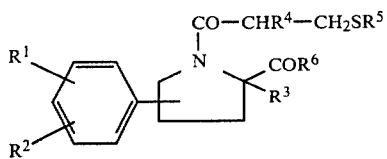

wherein $R^1$ and $R^2$ are, independently, hydrogen or alkoxy of one to three carbon atoms;

$R^3$ is hydrogen or methyl $R^4$ is hydrogen or alkyl of one to three carbon atoms;

$R^5$ is hydrogen, acetyl or benzoyl; and $R^6$ is —OH or —OM where M is a pharmaceutically acceptable cation.

3. A compound of claim 2 which is cis-1-(3-acetylthiopropanoyl)-5-(3,4-dimethoxyphenyl) proline or a pharmaceutically acceptable salt thereof.

4. A compound of claim 2 which is cis-1-(3-mercaptopropanoyl)-5-(3,4-dimethoxyphenyl) proline or a pharmaceutically acceptable salt thereof.

5. A compound of claim 2 which is cis-1-(benzoylthiopropanoyl)-5-phenyl proline or a pharmaceutically acceptable salt thereof.

6. A compound of claim 2 which is cis-1-(3-Mercaptopropanoyl)-5-phenyl proline or a pharmaceutically acceptable salt thereof.

7. A compound of claim 2 which is 5-phenyl-1-(3-benzoylthio-2-methylpropanoyl) proline.

8. A compound of claim 2 which is 5-phenyl-1-(3-mercapto-2-methylpropanoyl)proline.

* * * * *